United States Patent [19]

Edwards

[11] Patent Number: 4,652,558
[45] Date of Patent: Mar. 24, 1987

[54] 2-THIO-ORGANOTIN-4(3H)-QUINAZOLI-NONE

[75] Inventor: Laroy H. Edwards, Napa, Calif.

[73] Assignee: Chevron Research Company, San Francisco, Calif.

[21] Appl. No.: 833,947

[22] Filed: Feb. 27, 1986

Related U.S. Application Data

[63] Continuation-in-part of Ser. No. 749,617, Jun. 26, 1985, abandoned.

[51] Int. Cl.$^4$ .................... A01N 55/04; C07D 239/95
[52] U.S. Cl. .................................... 514/186; 544/225;
544/285
[58] Field of Search .................... 544/225; 514/186

[56] References Cited

U.S. PATENT DOCUMENTS 4,337,093  6/1982  Metzner et al. .................... 514/600

OTHER PUBLICATIONS

Meglitsch, "Invertebrate Zoology", 2nd Edition (1972), pp. 496–497.

Primary Examiner—Mark L. Berch
Attorney, Agent, or Firm—S. R. LaPaglia; R. C. Gaffney; S. L. Biggs

[57] ABSTRACT

Compounds of the formula:

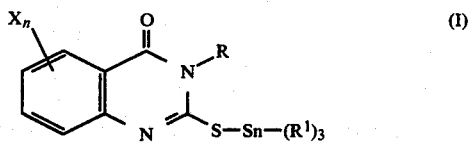

(I)

wherein X is independently halogen, lower alkyl of 1 to 6 carbon atoms, lower alkoxy of 1 to 6 carbon atoms, nitro, lower alkylsulfinyl of 1 to 6 carbon atoms, lower alkylthio of 1 to 6 carbon atoms, amino or trifluoromethyl; n is 0, 1, 2 or 3; R is hydrogen, alkyl of 1 to 10 carbon atoms, cycloalkyl of 3 to 8 carbon atoms, lower alkenyl of 2 to 6 carbon atoms, or lower alkynyl of 2 to 6 carbon atoms, all optionally substituted with 1 to 3 of the same or different halogen atoms; or aryl of 6 to 12 carbon atoms; or substituted aryl substituted with 1 to 3 substituents independently selected from lower alkyl of 1 to 4 carbon atoms, lower alkoxy of 1 to 4 carbon atoms, and the group —S(O)$_k$R$^2$ where k is 0, 1 or 2 and R$^2$ is lower alkyl of 1 to 4 carbon atoms, nitro, cyano or halogen; and R$^1$ is lower alkyl of 1 to 6 carbon atoms, lower cycloalkyl of 3 to 8 carbon atoms or aryl of 6 to 12 carbon atoms, provided that R and R$^1$ are not both cyclohexyl, are fungicidal and in some cases insecticidal.

39 Claims, No Drawings

2-THIO-ORGANOTIN-4(3H)-QUINAZOLINONE

CROSS-REFERENCE TO RELATED APPLICATIONS

This application is a continuation-in-part of U.S. Ser. No. 749,617, filed June 26, 1985, abandoned.

BACKGROUND OF THE INVENTION

The present invention relates to novel organotin derivatives of 4(3H)-quinazolinone compounds which are useful as fungicides.

Commonly-assigned U.S. patent application Ser. No. 306,796 "Algicidal and Fungicidal 2-Haloalkyl-3-oxo-4-Substituted Quinazaline" discloses compounds of the formula:

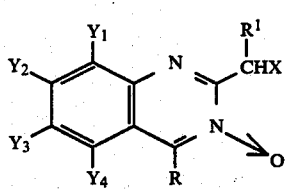

wherein R is hydrogen, lower alkyl, lower alkyl substituted with one to three of the same or different halogens, phenyl or phenyl substituted with 1 to 3 of the same or different substituents selected from a group consisting of lower alkyl, lower alkoxy, lower alkylthio, fluoro, chloro, bromo, iodo, nitro, cyano, or lower alkyl substituted with one to three of the same or different halogens, $R^1$ is hydrogen, lower alkyl, or lower alkyl substituted with one to three of the same or different halogens, $Y_1$, $Y_2$, $Y_3$ and $Y_4$ are independently selected from a group consisting of hydrogen, lower alkyl, lower alkoxy, lower alkylthio, fluoro, chloro, bromo, iodo, nitro, cyano, or lower alkyl substituted with one to three of the same or different halogens and X is fluoro, chloro, bromo, iodo, cyano, lower alkoxy, thiocyano, imidazolyl, and

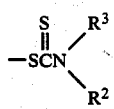

where $R^3$ and $R^2$ are the same or different lower alkyl, as fungicidal and algicidal.

My commonly-assigned U.S. patent application Ser. No. 728,997 "4-Quinazolone Fungicides" discloses fungicidal compounds of the formula:

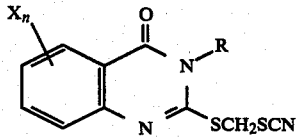

wherein X is independently halogen, lower alkyl of 1 to 6 carbon atoms, lower alkoxy of 1 to 6 carbon atoms, nitro, the group $R^1$—$S(O)_m$—wherein $R^1$ is lower alkyl of 1 to 6 carbon atoms and m is 0, 1 or 2, amino or trifluoro methyl; n is 0, 1, 2 or 3; R is alkyl of 1 to 10 carbon atoms, cycloalkyl of 3 to 8 carbon atoms, lower alkenyl of 2 to 6 carbon atoms or lower alkynyl of 2 to 6 carbon atoms, all optionally substituted with 1 to 3 of the same or different halogen atoms; aryl of 6 to 12 carbon atoms; or substituted aryl substituted with 1 to 3 substituents, independently selected from lower alkyl of 1 to 4 carbon atoms, lower alkoxy of 1 to 4 carbon atoms, lower alkylsulfinyl of 1 to 4 carbon atoms, lower alkyl sulfonyl of 1 to 4 carbon atoms, nitro, cyano or halogen.

SUMMARY OF THE INVENTION

The 4-(3H)-quinazolinone compounds of the present invention have the general formula:

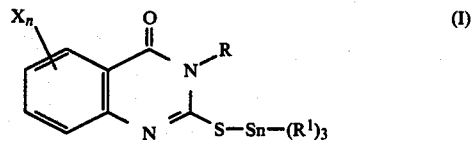

wherein X is independently halogen, lower alkyl of 1 to 6 carbon atoms, lower alkoxy of 1 to 6 carbon atoms, nitro, lower alkylsulfinyl of 1 to 6 carbon atoms, lower alkylthio of 1 to 6 carbon atoms, amino or trifluoromethyl; n is 0, 1, 2 or 3; R is hydrogen, alkyl of 1 to 10 carbon atoms, cycloalkyl of 3 to 8 carbon atoms, lower alkenyl of 2 to 6 carbon atoms, or lower alkynyl of 2 to 6 carbon atoms, all optionally substituted with 1 to 3 of the same or different halogen atoms; aryl of 6 to 12 carbon atoms; or substituted aryl substituted with 1 to 3 substituents independently selected from lower alkyl of 1 to 4 carbon atoms, lower alkoxy of 1 to 4 carbon atoms, and the group —$S(O)_kR^2$ where k is 0, 1 or 2 and $R^2$ is lower alkyl of 1 to 4 carbon atoms, nitro, cyano or halogen; and $R^1$ is lower alkyl of 1 to 6 carbon atoms, lower cycloalkyl of 3 to 8 carbon atoms or aryl of 6 to 12 carbon atoms provided that R and $R^1$ are not both cyclohexyl.

Among other factors, the present invention is based on my finding that these compounds are effective in controlling a variety of pests. In particular, these compounds are effective as fungicides and control certain plant fungal diseases. Some of these compounds are effective as insecticides. In addition, some of these compounds show herbicidal activity.

Preferred X groups include chloro, nitro, trifluoromethyl and methyl.

Preferred $R^1$ groups include hydrogen, phenyl and lower alkyl.

Preferred $R^1$ groups include phenyl.
Preferred halogens include chlorine.
Particularly preferred R groups include methyl.

Definitions

As used herein, the following terms have the following meanings unless expressly stated to the contrary.

The term "alkyl" refers to both straight- and branched-chain alkyl groups. The term "lower alkyl" refers to both straight- and branched-chain alkyl groups having a total of from 1 to 6 carbon atoms and includes primary, secondary and tertiary alkyl groups. Typical lower alkyls include, for example, methyl, ethyl, n-propyl, isopropyl, n-butyl, isobutyl, t-butyl, n-pentyl, n-hexyl, and the like.

The term "cycloalkyl" refers to cyclic alkyl groups. The term "lower cycloalkyl" refers to groups having from 3 to 6 carbon atoms in the ring, and includes cyclopropyl, cyclobutyl, cyclopentyl, and cyclohexyl.

The term "alkylene" refers to the group —(CH$_2$)$_m$— wherein m is an integer greater than zero. Typical alkylene groups include, methylene, ethylene, propylene and the like.

The term "alkylthio" refers to the group R'S- wherein R' is alkyl. The term "lower alkylthio" refers to alkylthio groups having 1 to 6 carbon atoms; examples include methylthio, ethylthio, n-hexylthio, and the like.

The term "alkoxy" refers to the group —OR' wherein R' is an alkyl group. The term "lower alkoxy" refers to alkoxy groups having from 1 to 6 carbon atoms; examples include methoxy, ethoxy, n-hexoxy, n-propoxy, isopropoxy, isobutoxy, and the like.

The term "alkenyl" refers to unsaturated alkyl groups having a double bond [e.g., CH$_3$CH=CH(CH$_2$)$_2$] and includes both straight- and branched-chain alkenyl groups. "Lower alkenyl" refers to groups having a total of from 2 to 6 carbon atoms. Typical lower alkenyl groups include, for example, vinyl, propenyl, but-3-enyl, hex-4-enyl, 2-methyl-pent-4-enyl, and the like.

The term "halo" or "halogen" refers to the groups fluoro, chloro, bromo and iodo.

The term "haloalkenyl" refers to alkenyl groups substituted with from 1 to 3 halogen atoms. "Lower haloalkenyl" refers to groups having a total of from 2 to 6 carbon atoms, and includes, for example, 1-chloropropenyl, 2,3-dibromo-but-3-enyl, and the like.

The term "alkynyl" refers to unsaturated alkyl groups having a triple bond (e.g., CH$_3$C≡CCH$_2$CH$_2$—) and includes both straight- and branched-chain alkynyl groups. "Lower alkynyl" refers to groups having a total of from 2 to 6 carbon atoms. Typical lower alkynyl groups include propynyl, but-3-ynyl, hex-4-ynyl, 2-methyl-pent-4-ynyl, and the like.

The term "hydroxy alkyl" refers to the group —R'—'OH wherein R'' is branched or unbranched alkylene and the hydroxy can be on a primary, secondary or a tertiary carbon. Examples include hydroxyethyl and 2-hydroxy-propyl and 2-hydroxy-2-methylbutyl.

The term "aryl" refers to aryl groups having from 6 to 12 carbon atoms and includes, for example, phenyl, p-chlorophenyl, m-methylphenyl, p-butylphenyl, m-trifluoromethylphenyl, naphthyl, and the like.

The term "aralkyl" refers to an alkyl group of 1 to 4 carbons substituted with an aryl group of from 6 to 12 carbons and includes, for example, benzyl, p-chlorobenzyl, p-methylbenzyl and 2-phenylethyl.

The term "alkylamino" refers to the group R'R''N— wherein R' is alkyl and R'' is hydrogen or alkyl. The term "lower alkylamino" refers to alkylamino groups having 1 to 6 carbon atoms. Typical alkylamino groups include methylamino, ethylamino, diethylamino, dimethylamino, and the like.

Pests are any insect, rodent, nematode, fungus, weed, or any form of terrestrial or aquatic plant or animal life or virus, bacterial organism or other microorganism (except those viruses, bacteria or other microorganisms existing in living humans or other living animals) considered injurious to health, the environment or man's economic well-being.

DETAILED DESCRIPTION OF THE INVENTION

The compounds of the present invention may be conveniently prepared according to the following synthetic scheme:

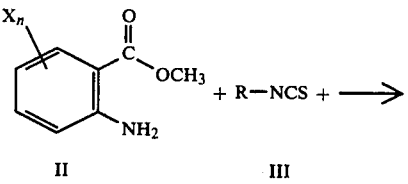

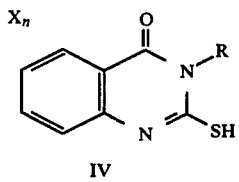

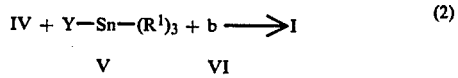

wherein X, n and R are as previously defined in conjunction with formula I, Y is halogen and b is a base.

Reaction (1) is conducted by combining approximately equimolar amounts of II and III in solvent. Optionally, an equivalent amount of a base such as triethylamine may be added as a catalyst. The reaction is conducted at a temperature of about 25° C. to about 100° C., preferably from about 80° C. to about 100° C. or at reflux, and is generally complete within about 8 to about 24 hours. The product, IV, is isolated by conventional procedures such as stripping, extraction, precipitation, filtration, chromatography, and the like. Suitable solvents include organic solvents such as dimethylformamide, methylene chloride, and the like.

Reaction (2) is conducted by combining approximately equimolar amounts of IV, V and VI in solvent. The reaction is conducted at a temperature of about 25° C. to about 40° C., preferably from about 35° C. to about 40° C. or, for convenience at reflux, and is generally complete in about 3 to about 6 hours. The product, I, is isolated by conventional procedures, such as stripping, extraction, trituration, precipitation, filtration, and the like. Suitable bases, b, include sodium hydride and organic bases such as triethylamine, pyridine and the like. Suitable solvents include inert organic solvents such as methylene chloride, dimethoxy ethane, and the like.

Utility

The compositions and methods of the present invention are useful in controlling a variety of pests, including certain plant fungal infections and in certain cases, insects, acarines and undesired vegetation.

These compounds are active as fungicides and are particularly effective in controlling a variety of fungi which are deleterious to plants, including plant fungal infections. These compounds are particularly effective in controlling leaf spot diseases. In particular, certain compounds are useful in controlling diseases caused by organisms such as *Aspergillus, Piricularia oryzae, Phytophthora infestans, Erysiphe polygoni* and *Fusarium*.

Some of these compounds are also effective as insecticides and acaricides and may be used in controlling a variety of insect and arthropod pests. In particular, some of these compounds are particularly effective in controlling acarines such as mites and lepidopterans such as cabbage loopers.

Like most insecticides and acaricides, the compounds are not usually applied full strength, but are generally incorporated with conventional biologically inert extenders or carriers normally employed for facilitating dispersion of active ingredients for agricultural chemical application, recognizing the accepted fact that the formulation and mode of application may affect the activity of a material. The toxicants of this invention may be applied as sprays, dusts, or granules to the insects, their environment or hostages susceptible to insect attack. It may be formulated as granules of large particle size, powdery dusts, wettable powders, emulsifiable concentrates, solutions, or as any of several other known types of formulations, depending on the desired mode of application.

Wettable powders are in the form of finely divided particles which disperse readily in water or other dispersants. These compositions normally contain from about 5% to 80% insecticide, and the rest inert material, which includes dispersing agents, emulsifying agents and wetting agents. The powder may be applied to the soil as a dry dust, or preferably as a suspension in water. Typical carriers include fuller's earth, kaolin clays, silicas, and other highly absorbent, readily wettable, inorganic diluents. Typical wetting, dispersing or emulsifying agents include, for example: the aryl and alkylaryl sulfonates and their sodium salts; alkylamide sulfonates, including fatty methyl taurides; alkylaryl polyether alcohols, sulfated higher alcohols and polyvinyl alcohols; polyethylene oxides; sulfonated animal and vegetable oils; sulfonated petroleum oils; fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises from 1% to 15% by weight of the insecticidal composition.

Dusts are freely flowing admixtures of the active insecticide with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about 50 microns. A typical dust formulation useful herein contains 75% silica and 25% of toxicant.

Useful liquid concentrates include the emulsifiable concentrates, which are homogeneous liquid or paste compositions which are readily dispersed in water or other dispersant, and may consist entirely of the insecticide with a liquid or solid emulsifying agent, or may also contain a liquid carrier such as xylene, heavy aromatic naphthas, isophorone, and other nonvolatile organic solvents. For application, these concentrates are dispersed in water or other liquid carrier, and are normally applied as a spray to the area to be treated.

Other useful formulations for insecticidal applications include simple solutions of the active insecticide in a dispersant in which it is completely soluble at the desired concentration, such as acetone, alkylated naphthalenes, xylene, or other organic solvents. Granular formulations, wherein the insecticide is carried on relatively coarse particles, are of particular utility for aerial distribution or for penetration of cover-crop canopy. Pressurized sprays, typically aerosols wherein the active ingredient is dispersed in finely divided form as a result of vaporization of a low-boiling dispersant solvent carrier, such as the Freons, may also be used. All of those techniques for formulating and applying insecticides are well known in the art.

The percentages by weight of the insecticide may vary according to the manner in which the composition is to be applied and the particular type of formulation, but in general comprise 0.5% to 95% of the toxicant by weight of the insecticidal composition.

The insecticidal compositions may be formulated and applied with other active ingredients, including nematocides, insecticides, fungicides, bactericides, plant-growth regulators, fertilizers, etc. In applying the chemical, an effective amount and concentration of the toxicant of this invention is, of course, employed.

When used as a fungicide, the compounds of the invention are applied in fungicidally effective amounts to fungi and/or their habitats, such as vegetative hosts and non-vegetative hosts, e.g., animal products. The amount used will, of course, depend on several factors such as the host, the type of fungus, and the particular compound of the invention. As with most pesticidal compounds, the fungicides of the invention are not usually applied full strength, but are generally incorporated with conventional, biologically inert extenders or carriers normally employed for facilitating dispersion of active fungicidal compounds, recognizing that the formulation and mode of application may affect the activity of the fungicide. Thus, the fungicide of this invention may be formulated and applied as granules, as powdery dusts, as wettable powders, as emulsifiable concentrates, as solutions, or as any of several other known types of formulations, depending on the desired mode of application.

Wettable powders are in the form of finely divided particles which disperse readily in water or other dispersants. These compositions normally contain from about 5% to 80% fungicide, and the rest inert material, which includes dispersing agents, emulsifying agents and wetting agents. The powder may be applied to the soil as a dry dust, or preferably as a suspension in water. Typical carriers include fuller's earth, kaolin clays, silicas, and other highly absorbent, readily wettable, inorganic diluents. Typical wetting, dispersing or emulsifying agents include, for example: the aryl and alkylaryl sulfonates and their sodium salts; alkylamide sulfonates, including fatty methyl taurides; alkylaryl polyether alcohols, sulfated higher alcohols and polyvinyl alcohols; polyethylene oxides; sulfonated animal and vegetable oils; sulfonated petroleum oils; fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises from 1% to 15% by weight of the fungicidal composition.

Dusts are freely flowing admixtures of the active fungicide with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about 50 microns. A typical dust formulation useful herein contains 75% silica and 25% of toxicant.

Useful liquid concentrates include the emulsifiable concentrates, which are homogeneous liquid or paste compositions which are readily dispersed in water or other dispersant, and may consist entirely of the fungicide with a liquid or solid emulsifying agent, or may also contain a liquid carrier such as xylene, heavy aromatic naphthas, isophorone, and other nonvolatile organic solvents. For application, these concentrates are dispersed in water or other liquid carrier, and are normally applied as a spray to the area to be treated.

Other useful formulations for fungicidal applications include simple solutions of the active fungicide in a dispersant in which it is completely soluble at the desired concentration, such as acetone, alkylated naphthalenes, xylene, or other organic solvents. Granular formulations, wherein the fungicide is carried on relatively coarse particles, are of particular utility for aerial distribution or for penetration of cover-crop canopy. Pressurized sprays, typically aerosols wherein the active ingredient is dispersed in finely divided form as a result of vaporization of a low-boiling dispersant solvent carrier, such as the Freons, may also be used. All of those techniques for formulating and applying fungicides are well known in the art.

The percentages by weight of the fungicide may vary according to the manner in which the composition is to be applied and the particular type of formulation, but in general comprise 0.5% to 95% of the toxicant by weight of the fungicidal composition.

The fungicidal compositions may be formulated and applied with other active ingredients, including other fungicides, insecticides, nematocides, bactericides, plant-growth regulators, fertilizers, etc.

A particularly preferred embodiment for the herbicidal compositions is as a wettable powder. The wettable powder desirably contains the above-mentioned herbicidally-active compound and an inert carrier such as kaolin clay, talc, atapulgite, calcium carbonate or magnesium carbonate. Kaolin clay is an especially preferred inert carrier. Also, desirably the composition contains a surfactant or dispersing agent such as are known in the art for aiding the dispersion of the finely-divided powder ingredients of the composition in a solvent such as water. The surfactant may be of the nonionic type or the ionic type and can be selected from materials such as calcium alkyl sulfonates or sodium lauryl sulfonate, or a lignosulfonate salt.

Preferred amounts of the ingredients of the composition are 1-90% active compound, 10-95% inert carrier and 0.5-15% surfactant. More preferred ranges are 10-80% active, 20-90% inert carrier and 1-9% surfactant. Particularly preferred wettable powder herbicidal compositions of the present invention contain about 40-60% active, 40-60% inert carrier and 2-8% surfactant. Percentages in this specification are by weight unless indicated otherwise.

The herbicidal composition of the present invention may alternatively be formulated as a "flowable" with either an oil or water base. In the instance of a flowable herbicidal composition, the oil or water base is considered, for purposes of the present specification, as the inert carrier. Desirably, the flowable composition will also contain a suspending agent or thickener. Types of suspending agents known in the art include the following: density suspension, clay suspension, polymer suspension or surfactant suspension.

Preferably, the flowable herbicidal composition in accordance with the present invention contains 20-70% active, 30-80% inert carrier (oil or water base), and 1-10% suspending agent.

In the case of either the wettable powder or the flowable herbicidal composition of the present invention, preferably the active compound is micronized; that is, very finely divided into particle sizes between about 0.5 and 20 microns, more preferably between 2 and 8 microns, for purposes of formulating the final herbicidal composition.

Preferred amounts of the fungicidal, insecticidal and acaricidal compositions are from about 0.5 to about 95% by weight active compound (ingredient), from about 5 to about 99.5% inert carrier and about 0 to about 20% of a surfactant.

A further understanding of the invention can be had in the following non-limiting Examples. Wherein, unless expressly stated to the contrary, all temperature ranges refer to the Centigrade system and the term "ambient" or "room temperature" refers to about 20° C. to about 25° C. The term "percent" refers to gram moles. The term "equivalent" refers to a quantity of reagent equal in moles, to the moles of the preceding or succeeding reagent recited in that example in terms of finite moles or finite weight or volume. Also, unless expressly stated to the contrary, geometric isomer and racemic mixtures are used as starting materials and correspondingly, isomer mixtures are obtained as products.

EXAMPLES

EXAMPLE 1

Preparation of
2-Mercapto-3-phenyl-4(3H)-quinazolinone

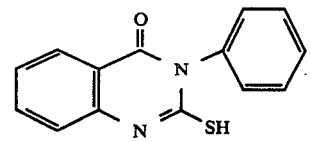

In a 500-ml, three-neck round bottom flask, equipped with magnetic stirrer, 25 g (0.17 moles) methyl anthranilate in 100 ml methylene chloride was placed. Into that mixture 23.0 g (0.17 moles) phenyl isothiocyanate in 50 ml methylene chloride was dropped in. The reaction mixture was stirred overnight (at ambient temperature). The reaction mixture was refluxed at 40° C. for one hour. Ether (about 50 ml) was added; a precipitate formed which was removed by suction filtration to give the above-identified product.

EXAMPLE 2

Preparation of
3-Phenyl-2-tri-n-butyl-stannylthio-4(3H)-quinazolinone

To a stirred solution of 4 g (0.01 mole) 2-mercapto-3-phenyl-4(3H)-quinazolinone (the product of Example 1) and 4.6 g (0.014 mole) tributyl tin chloride in methylene chloride (about 75 ml), 1.4 g (0.014 mole) triethyl amine in methylene chloride (about 25 ml) was added dropwise. The reaction mixture was stirred for about one hour at ambient temperature, refluxed about three hours, stirred overnight, refluxed about eight hours and again stirred overnight. The reaction mixture was washed with water. The organic fraction was dried over magnesium sulfate and stripped to give the above-identified product as an oil.

Elemental analysis for $C_{26}H_{38}N_2OSSn$ showed: calculated % C 57.3, % H 7.01, and % N 5.14; found % C 51.31, % H 6.93, and % N 3.35.

EXAMPLE 3

Preparation of 7-Chloro-2-mercapto-3-phenyl-4(3H)-quinazolinone

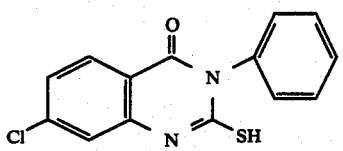

A mixture of 25 g (0.15 mole) 4-chloroanthranilic acid and 20.3 g (0.15 mole) phenyl isocyanate in dimethylformamide (about 100 ml) was stirred for about 30 minutes at ambient temperature, refluxed 3 hours, stirred at ambient temperature, refluxed for 4.5 hours and then cooled. The reaction mixture was poured into water, then ice was added. The resulting mixture was stirred by hand and then filtered. The solid was dissolved in methylene chloride; the resulting mixture was dried and stripped to give a residue. Crystallization of the residue from ethanol gave 18.1 g of the above-identified product as a crystalline solid.

EXAMPLE 4

Preparation of 7-Chloro-3-phenyl-2-triphenylstannylthio-4(3H)-quinazolinone

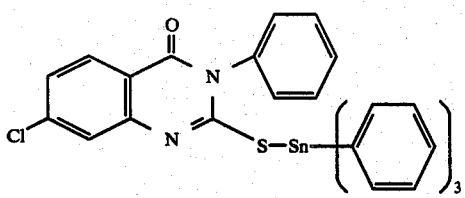

To a stirred mixture of 4 g (0.014 mole) 7-chloro-2-mercapto-3-phenyl-4(3H)-quinazolinone (the product of Example 3) and 5.4 g (0.014 mole) chlorotriphenyl tin in methylene chloride (about 75 ml), 1.4 g (0.014 mole) triethylamine in methylene chloride (about 25 ml) was added dropwise. The resulting mixture was stirred for about one hour at ambient temperature, refluxed about 5 hours, stirred overnight, refluxed about 4 hours and cooled. The mixture was washed with water. The organic fraction was dried and stripped to give the above-identified product as a solid, melting point 110° to 112° C.

Elemental analysis for $C_{32}H_{23}ClN_2OSSn$ showed: calculated % C 60.27, % H 3.63, and % N 4.40; found % C 52.4, % H 3.37, and % N 3.36.

EXAMPLE 5

Preparation of 3-Allyl-2-mercapto-4(3H)-quinazolinone

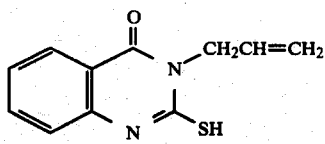

To a stirred mixture of 50 g (0.33 mole) methyl anthranilate in 100 ml methylene chloride, 32.7 g (0.33 mole) allyl isothiocyanate in 50 ml methylene chloride was added dropwise. The reaction mixture was refluxed at 40° C. one hour, stirred over the weekend at ambient temperature, and refluxed at 40° C. for one hour. The reaction mixture was stripped. Additional methylene chloride (200 ml) was added; the resulting mixture was refluxed at 40° C. for 7 hours, and then stirred about 1½ days at ambient temperature. The reaction mixture was stripped. Ether was added; a precipitate formed. The above-identified product was isolated by suction filtration.

EXAMPLE 6

Preparation of 3-n-Butyl-2-mercapto-4(3H)-quinazolinone

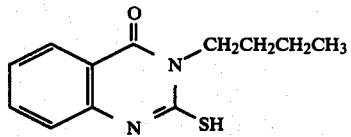

A stirred mixture of 7.6 g (0.05 mole) methyl anthranilate and 5.8 g (0.05 mole) n-butyl isothiocyanate in 45 ml dimethylformamide was heated at reflux for 1½ hours, stirred overnight, then heated for 6 hours and then stirred at ambient temperature over the weekend. The reaction mixture was poured into 200 ml water (at 20° C.) to give a precipitate. The mixture was chilled and then filtered. The precipitate was washed three times with water; the filtrate was set aside. A small amount of ethanol was drained through the filter cake once. The solid was washed twice with hexane and air-dried overnight to give the above-identified product, as a solid, melting point 167°–172° C.

EXAMPLE 7

Preparation of 3-n-Butyl-2-triphenylstannylthio-4(3H)-quinazolinone

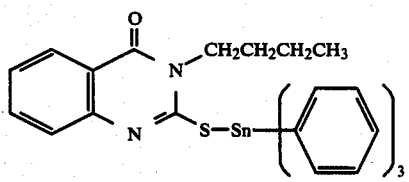

A mixture of 0.85 g (0.004 mole) 3-n-butyl-2-mercapto-4(3H)-quinazolinone (the product of Example 6), 1.54 g (0.004 mole) chlorotriphenyl tin and 0.4 g (0.004 mole) triethylamine in methylene chloride (about 100 ml) was stirred for one hour, refluxed 5.5 hours, stirred overnight and refluxed 8 hours. The reaction mixture was washed with water. The organic phase was dried over magnesium sulfate, and stripped to obtain the above-identified product as a solid, melting point 112° to 114° C.

Elemental analysis for $C_{30}H_{28}N_2OSSn$ showed: calculated % C 61.8, % H 4.8, and % N 4–8; found % C 62.63, % H 5.29, and % N 4.36.

EXAMPLE 8

Preparation of 3-Methyl-2-triphenylstannylthio-4(3H)-quinazolinone

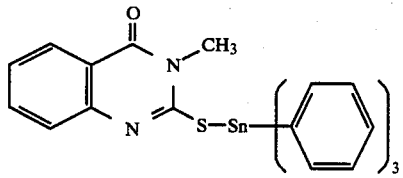

A mixture of 11.6 g (0.06 mole) 3-methyl-2-mercapto-4(3H)-quinazolinone, 23.2 g (0.06 mole) chlorotriphenyl tin and 6.1 g (0.06 mole) triethylamine in methylene chloride (about 200 ml) were stirred together, then refluxed for four hours and stirred overnight. The reaction mixture was washed with water, dried and stripped. After trituration with ether, 20.0 g of the above-identified product as a white solid, melting point 155°–157° C. was obtained.

Compounds made in accordance with the methods disclosed in the Detailed Description of the Invention and with Examples 1 to 8 are found in Table I.

In addition, by following the procedures disclosed in the Detailed Description of the Invention and Examples 1 to 8 and using the appropriate starting materials and reagents, the following compounds are made:
2-Tributylstannylthio-4(3H)-quinazolinone;
2-Tricyclohexylstannylthio-4(3H)-quinazolinone;
3-Allyl-7-chloro-2-triphenylstannylthio-4(3H)-quinazolinone;
3-Allyl-7-chloro-2-tributylstannylthio-4(3H)-quinazolinone;
3-Allyl-7-chloro-2-tricyclohexylstannylthio-4(3H)-quinazolinone;
3-N-butyl-2-tributylstannylthio-4(3H)-quinazolinone;
3-N-butyl-2-tricyclohexylstannylthio-4(3H)-quinazolinone;
3-Cyclohexyl-2-tributylstannylthio-4(3H)-quinazolinone;
7-Chloro-2-triphenylstannylthio-4(3H)-quinazolinone;
7-Chloro-2-tributylstannylthio-4(3H)-quinazolinone;
7-Chloro-2-tricyclohexylstannylthio-4(3H)-quinazolinone;
7-Chloro-3-methyl-2-triphenylstannylthio-4(3H)-quinazolinone;
7-Chloro-3-methyl-2-tributylstannylthio-4(3H)-quinazolinone;
7-Chloro-3-methyl-2-tricyclohexylstannylthio-4(3H)-quinazolinone;
3-n-Butyl-7-chloro-2-triphenylstannylthio-4(3H)-quinazolinone;
3-n-Butyl-7-Chloro-2-tributylstannylthio-4(3H)-quinazolinone;
3-n-Butyl-7-Chloro-2-tributylstannylthio-4(3H)-quinazolinone;
3-p-Methoxyphenyl-2-tributylstannylthio-4(3H)-quinazolinone;
3-tert-Butyl-2-triphenylstannylthio-4(3H)-quinazolinone;
3-tert-Butyl-2-tributylstannylthio-4(3H)-quinazolinone;
3-tert-Butyl-2-tricyclohexylstannylthio-4(3H)-quinazolinone;
3-n-Hexyl-2-triphenylstannylthio-4(3H)-quinazolinone;
3-n-Hexyl-2-tributylstannylthio-4(3H)-quinazolinone;
3-n-Hexyl-2-tricyclohexylstannylthio-4(3H)-quinazolinone;
3-n-Butyl-7-trifluoromethyl-2-triphenylstannylthio(4(3H)-quinazolinone;
3-n-Butyl-2-tributylstannylthio-7-trifluoromethyl(4(3H)-quinazolinone;
3-n-Butyl-2-tricyclohexylstannylthio-7-trifluoromethyl-4(3H)-quinazolinone;
3-Phenyl-7-trifluoromethyl-2-triphenylstannylthio(4(3H)-quinazolinone; 3-Phenyl-2-tributylstannylthio-7-trifluoromethyl(4(3H)-quinazolinone;
3-Phenyl-2-tricyclohexylstannyl-7-trifluoromethyl(4(3H)-quinazolinone;
6-Nitro-3-phenyl-2-triphenylstannylthio-4(3H)-quinazolinone;
6-Nitro-3-phenyl-2-tributylstannylthio-4(3H)-quinazolinone;
6-Nitro-3-phenyl-2-tricyclohexylstannylthio-4(3H)-quinazolinone;
7-Methyl-3-phenyl-2-triphenylstannylthio-4(3H)-quinazolinone;
7-Methyl-3-phenyl-2-tributylstannylthio-4(3H)-quinazolinone;
7-Methyl-3-phenyl-2-tricyclohexylstannylthio-4(3H)-quinazolinone;
3-(Propen-2-yl)-2-triphenyl-stannylthio-4(3H)-quinazolnone;
3-(Propen-2-yl)-2-tributylstannylthio-4(3H)-quinazolinone; and
3-(Propen-2-yl)-2-tricyclohexylstannylthio-4(3H)-quinazolinone.

EXAMPLE A

Bacterial Inhibition

Compounds of this invention were evaluated for in vitro bactericidal effectiveness by means of a bacterial inhibition test. This test is designed to measure the antibacterial activity of compounds in terms of degree of inhibition bacterial multiplication. The representative bacteria used were *Erwinia amylovora, Pseudomonas syringae* and *Xanthomonas vesicatoria*. Each compound to be tested was dissolved in acetone to give a 500 ppm concentration. Agar plates were inoculated using a micro sprayer with an suspension of the particular bacteria shortly (3 to 5 seconds) before treatment. The inoculated agar plates were then treated with the compound to be tested by spraying with a micro sprayer. The treated plates were incubated at 23.5° C. and the data was taken 24 hours after treatment. Antibacterial activities are measured by a zone of inhibited bacterial growth from the center of the agar plate and the deposit concentration in $mg/cm^2$ at the edge of the zone of inhibition ($ED_{99}$). The effectiveness of the compounds for antibacterial activity are reported in Table II in terms of the percent of the $ED_{99}$ of each compound of the $ED_{99}$ of the standard PMA (phenyl mercuric acetate).

EXAMPLE B

Mycelial Inhibition

Compounds were evaluated for in vitro fungicidal effectiveness by means of a mycelial inhibition test. This test is designed to measure the fungitoxic activity of fungicidal chemicals in terms of their degree of inhibition of mycelium growth. Fungi used were *Pythium ultimum, Rhizoctonia solani, Fusarium moniloforme, Botrytis cinerea, Aspergillus niger* and *Ustilago hordeii*. Each compound to be tested was dissolved in acetone to 500-ppm concentration. Paper strips were infused with the particular mycelium growth by covering the paper with a potato dextrose broth culture of mycelial suspension. The papers were then placed on potato dextrose agar plates and sprayed by means of a micro sprayer with the fungicidal solution. The treated paper strips were incubated at 25° C. and the data is taken after 24 hours. Fungicidal activities are measured by a zone of inhibited mycelial growth from the center of the paper strip in terms of mg/cm² needed for 99% control of the fungus ($ED_{99}$). The effectiveness of the compounds for fungicidal activity are reported in Table III in terms of the percent of the $ED_{99}$ of the test compound of the $ED_{99}$ of the standard Difolatan ®.

EXAMPLE C

Tomato Late Blight

Compounds were tested for the preventative control of the Tomato Late Blight organism *Phytophthora infestans*. Five- to six-week-old tomato (cultivar Bonny Best) seedlings were used. The tomato plants were sprayed with a 200-ppm suspension of the test compound in acetone, water and a nonionic emulsifier. The sprayed plants were then inoculated 1 day later with the organism, placed in an environmental chamber and incubated at 66° F. to 68° F. and 100% relative humidity for at least 16 hours. Following the incubation, the plants were maintained in a greenhouse for approximately 7 days. The percent disease control provided by a given test compound was based on the percent disease reduction relative to untreated check plants. The results are tabulated in Table III.

EXAMPLE D

Rice Blast

Compounds of this invention were tested for control of the Rice Blast organism *Piricularia oryzae*, using 10- to 14-day-old rice plant seedlings (Calrose M-9 variety). Seedling plants were sprayed with a 625-ppm solution of the test compound in acetone, water and a nonionic emulsifier (ORTHO X-77 spreader). The sprayed plants were inoculated 1 day later with the organism in an environmental chamber. After inoculation, the plants were kept in an environmental chamber for about 48 hours under conditions of about 72° F. to 75° F. and about 100% relative humidity. Following the incubation period, the plants were placed in a greenhouse with a temperature of about 72° F. and maintained with bottom watering for about 12 to 16 days. The percent disease control provided by a given test compound is based on a comparison of the percentage disease relative to the percent disease development on the untreated check plants:

$$\% \text{ Control} = 100 - 100 \times \left( \frac{\% \text{ disease in treated plants}}{\% \text{ disease in check}} \right)$$

The results are tabulated in Table III.

EXAMPLE E

Tomato Early Blight

Compounds were tested for the control of the Tomato Early Blight organism *Alternaria solani*. Tomato (variety Bonny Best) seedlings of 6- to 7-weeks old were used. The tomato plants were sprayed with a 200-ppm solution of the test compound in an acetone-and-water solution containing a small amount of a nonionic emulsifier. The sprayed plants were inoculated 1 day later with the organism, placed in the environmental chamber and incubated at 66° F. to 68° F. and 100% relative humidity for 24 hours. Following the incubation, the plants were maintained in a greenhouse for about 12 days. Percent disease control was based on the percent disease development on untreated check plants. The results are tabulated in Table III.

EXAMPLE F

Celery Late Blight

The Celery Late Blight tests were conducted using celery (Utah) plants 11 weeks old. The Celery Late Blight organism was *Septoria apii*. The celery plants were sprayed with 200-ppm solutions of the candidate toxicant mixed with acetone, water and a nonionic emulsifier. The plants were then inoculated with the organism and placed in an environmental chamber and incubated at 66° F. to 68° F. in 100% relative humidity for an extended period of time (approximately 48 hours). Following the incubation, the plants were allowed to dry and then were maintained in a greenhouse for approximately 14 days. The percent disease control provided by a given test compound is based on the percent disease reduction relative to untreated check plants. The results are reported in Table III.

EXAMPLE G

Bean Powdery Mildew

Compounds were tested for the control of the Bean Powdery Mildew organism *Erysiphe polygoni*. Seedling bean plants were sprayed with a 250-ppm solution of the test compound in acetone, water and a nonionic emulsifier. The sprayed plants were then inoculated 1 day later with the organism. The plants were maintained for 10 days at temperatures of 68° F. at night with daytime temperatures of 72° F. to 80° F.; relative humidity was maintained at 40% to 60%. The percent disease control provided by a given test compound was based on the percent disease reduction relative to the untreated check plants. The results as percent control are tabulated in Table III.

EXAMPLE H

Bean Rust

Compounds were evaluated for their ability to eradicate Bean Rust caused by *Uromyces phaseoli typica* on pinto beans.

Pinto bean plants, variety Idaho 1-11, 16 (summer) or 19 (winter) days old were inoculated with a 50-ppm suspension of uredospores in water containing a small amount of nonionic surfactant. The inoculated plants were placed in an environmental chamber immediately after inoculation and incubated 20 hours. Following the incubation period, the plants were removed from the chamber and placed in a greenhouse maintained at 66°–68° F. and 60–80% relative humidity. Two days after inoculation, the plants were treated by spraying with a 200-ppm solution of test compound in an acetone and water carrier formulation containing a small amount of nonionic surfactant. One or two replicate pots (each containing two plants) were used for each compound. In addition one or two replicate pots were sprayed with the same carrier formulation (without a test compound) as a control (hereinafter "untreated Checks"). The plants were kept in the greenhouse until evaluated. The plants were evaluated for disease control when disease symptoms were well developed on the untreated Checks, normally about 14 days after treatment. The percentage disease control (or eradication) provided by a test compound was based on the percent disease reduction relative to the untreated Checks. The results are reported in Table III.

EXAMPLE I

Aphid Control

The compounds of this invention were tested for their insecticidal activity against cotton aphids (*Aphis gossypii* Glover). An acetone solution of the test compound containing a small amount of nonionic emulsifier was diluted with water to give a concentration of 40 ppm. Cucumber leaves infested with cotton aphids were dipped in the test compound solution. Mortality readings were taken after 24 hours. The results are tabulated in Table II in terms of percent control.

EXAMPLE J

Aphid Systemic Evaluation

This procedure is used to assess the ability of a candidate insecticide to be absorbed through the plant root system and translocate to the foliage and thus to show insecticidal activity against the cotton aphid (*Aphis gossypii* Glover).

Two cucumber plants planted in a 4-inch fiber pot with a soil surface area of 80 cm² are used. Forty ml of an 80-ppm solution of the candidate insecticide is poured around the plants in each pot. (This corresponds to 40 gamma/cm² of actual toxicant.) The plants are maintained throughout in a greenhouse at 75°–85° F. Forty-eight hours after the drenching, the treated plants are infested with aphids by placing well-colonized leaves over the treated leaves so as to allow the aphids to migrate easily from the inoculated leaf to the treated leaf. Three days after infestation, mortality readings were taken. The results are tabulated in Table IV in terms of percent control.

EXAMPLE K

Mite Adult

Compounds of this invention were tested for their insecticidal activity against parathion-resistant Two-spotted Spider Mite (*Tetranychus urticae* Koch). An acetone solution of the candidate toxicant containing a small amount of nonionic emulsifier was diluted with water to 40 ppm. Lima bean leaves which were infested with mites were dipped in the toxicant solution. The results are tabulated in Table IV in terms of percent control.

EXAMPLE L

Mite Egg Control

Compounds of this invention were tested for their ovicidal activity against eggs of the two-spotted spider mite (*Tetranychus urticae* Koch). An acetone solution of the test toxicant containing a small amount of nonionic emulsifier was diluted with water to give a concentration of 40 ppm. Two days before testing, 2-week old lima bean plants were infested with spider mites. Two days after infestation, leaves from the infested plants are dipped in the toxicant solution, placed in a petridish with filter paper and allowed to dry in the open dish at room temperature. The treated leaves were then held in covered dishes at about 31° C. to 33° C. for seven days. On the eighth day egg mortality readings are taken. The results, expressed as percent control, are tabulated in Table IV.

EXAMPLE M

Housefly

Compounds of this invention were tested for their insecticidal activity against the Housefly (*Musca domestica* Linnaeus). A 500-ppm acetone solution of the candidate toxicant was placed in a micro sprayer (atomizer). A random mixture of anesthetized male and female flies was placed in a container and 55 mg of the above-described acetone solution was sprayed on them. A lid was placed on the container. A mortality reading was made after 24 hours. The results are tabulated in Table IV in terms of percent control.

EXAMPLE N

American Cockroach

Compounds of this invention were tested for their insecticidal activity against Chlorodane-resistant American Cockroaches (*Periplaneta americana* Linnaeus). A 500-ppm acetone solution of the candidate toxicant was placed in a micro sprayer (atomizer). A random mixture of anesthetized male and female roaches was placed in a container and 55 mg of the above-described solution was sprayed on them. A lid was placed on the container. A mortality reading was made after 24 hours. The results are tabulated in Table IV in terms of percent control.

EXAMPLE O

Alfalfa Weevil

The compounds of this invention were tested for their insecticidal activity against Alfalfa Weevil (*Hypera brunneipennis* Boheman). A 500-ppm acetone solution of the candidate toxicant was placed in a micro sprayer (atomizer). A random mixture of male and female weevils was placed in a container and 55 mg of the above-described acetone solution was sprayed on them. A lid was placed on the container. A mortality reading was made after 24 hours. The results are tabulated in Table IV in terms of percent control.

EXAMPLE P

Cabbage Looper Control

The compounds of this invention were tested for their insecticidal activity against Cabbage Looper (*Trichoplusia ni* Hubner). An acetone solution of the candidate toxicant containing a small amount of nonionic emulsifier was diluted with water to give a concentration of 500 ppm. Excised cucumber leaves were dipped in the toxicant solution and allowed to dry. The leaves were then infested with Cabbage Looper larvae. Mortality readings were taken after 24 hours. The results are tabulated in Table IV in terms of percent control.

EXAMPLES Q AND R

The compound was respectively tested for pre-emergent and post-emergent activity against a variety of grasses and broad-leaf plants including one grain crop and one broad-leaf crop.

EXAMPLE Q

Pre-Emergent Herbicide Test

Pre-emergence herbicidal activity was determined in the following manner.

An acetone solution of the test compound was prepared by mixing 750 mg of the test compound, 220 mg of a nonionic surfactant and 25 ml of acetone. This solution was added to approximately 125 ml of water containing 156 mg of surfactant.

Seeds of the test vegetation were planted in a pot of soil and the test compound solution was sprayed uniformly onto the soil surface at a dose of 27.5 micrograms/cm². The pot was watered and placed in a greenhouse. The pot was watered intermittently and was observed for seedling emergence, health of the emerging seedlings, etc., for a 3-week period. At the end of this period the herbicidal effectiveness of the test compound was rated based on the physiological observations. A 0-to-100-scale was used, 0 representing no phytotoxicity and 100 representing complete kill. The results of these tests are summarized in Table V, hereinbelow.

EXAMPLE R

Post-Emergent Test

The test compound was formulated in the same manner as described above for the pre-emergent test. The concentration of the test compound in this formulation was 5000 ppm. This formulation was uniformly sprayed on 2 similar pots of 24-day-old plants (approximately 15 to 25 plants per pot) at a dose of 27.5 micrograms/cm². After the plants had dried, they were placed in a greenhouse and then watered intermittently at their bases, as needed. The plants were observed periodically for phytotoxic effects and physiological and morphological responses to the treatment. After 3 weeks, the herbicidal effectiveness of the compound was rated based on these observations. A 0-to-100-scale was used, 0 representing no phytotoxicity and 100 representing complete kill. The results of these tests are summarized in Table V.

TABLE I

Compounds of the Formula:

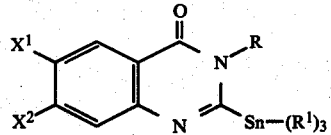

| Compound No. | $X^1$ | $X^2$ | R | $R^1$ | Physical State | %C Calc. | %C Found | %H Calc. | %H Found | %N Calc. | %N Found |
|---|---|---|---|---|---|---|---|---|---|---|---|
| 1  46169 | —H | —H | —H |  | White Solid, mp above 260° C. | 59.23 | 52.15 | 3.82 | 3.81 | 5.31 | 6.31 |
| 2  46388 | —H | —H | —CH₃ | —(CH₂)₃CH₃ | Orange oil | 52.41 | 50.25 | 7.12 | 8.26 | 5.82 | — |
| 3  46360 | —H | —H | —CH₃ |  | Yellow Solid, mp 95–97° C. | 57.99 | 58.8 | 7.21 | 8.58 | — | — |
| 4  46359 | —H | —H | —CH₃ |  | Yellow Solid, mp 155–157° | 59.92 | 61.22 | 4.09 | 4.36 | 5.17 | 3.8 |
| 5  45331 | —H | —H | —(CH₂)₃CH₃ |  | Crystalline solid, mp 112–116° C. | 61.8 | 62.63 | 4.8 | 5.29 | 4.8 | 4.36 |
| 6  45330 | —H | —H |  |  | Crystalline solid, mp 266–268° C. | 61.2 | 61.41 | 7.7 | 6.6 | — | — |

TABLE I-continued

Compounds of the Formula:

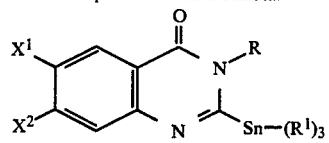

| Compound No. | X¹ | X² | R | R¹ | Physical State | %C Calc. | %C Found | %H Calc. | %H Found | %N Calc. | %N Found |
|---|---|---|---|---|---|---|---|---|---|---|---|
| 7 45228 | —H | —H | (thiophene) | (phenyl) | White solid, mp 135–138° C. | 63.07 | 64.46 | 4.96 | 5.18 | 4.60 | 4.29 |
| 8 46358 | —H | —H | —CH₂CH=CH₂ | —(CH₂)₃CH₃ | Yellow Oil | 54.45 | 51.16 | 7.15 | 6.85 | 5.52 | 4.41 |
| 9 46357 | —H | —H | —CH₂CH=CH₂ | (thiophene) | Yellow Solid, mp 104–106° C. | 59.5 | 59.5 | 7.23 | 6.75 | 4.78 | 4.61 |
| 10 46356 | —H | —H | —CH₂CH=CH₂ | (phenyl) | Yellow Solid, mp 96–98° C. | 61.4 | 61.92 | 4.26 | 4.68 | 4.94 | 5.21 |
| 11 45916 | —H | —H | (phenyl) | —(CH₂)₃CH₃ | Pale yellow oil mp 238–239° C. | 57.48 | — | 6.67 | — | 5.16 | — |
| 12 45915 | —H | —H | (phenyl) | (thiophene) | White solid, mp 108–110° C. | 61.85 | — | 6.81 | — | 4.51 | — |
| 13 45913 | —H | —H | (phenyl) | (phenyl) | White solid, mp 197–149° C. | 66.81 | — | 4.20 | — | 4.87 | — |
| 14 45301 | —H | —H | (4-OCH₃-phenyl) | (thiophene) | White solid, mp 233–235° C. | 60.84 | 61.29 | 6.81 | 7.29 | 4.30 | 4.24 |
| 15 45300 | —H | —H | (4-OCH₃-phenyl) | (phenyl) | White solid, mp 238–239° C. | 62.58 | 61.58 | 4.14 | 4.36 | 4.42 | 4.08 |
| 16 46151 | —H | —Cl | (phenyl) | —(CH₂)₃CH₃ | Amber Oil | 54.10 | 50.17 | 6.10 | 6.85 | 4.85 | 3.34 |
| 17 46150 | —H | —Cl | (phenyl) | (thiophene) | Yellow solid, mp 195–197° C. | 71.60 | 67.87 | 7.7 | 6.36 | 5.21 | 6.41 |
| 18 46166 | —H | —Cl | (phenyl) | (phenyl) | Yellow solid, mp 110–112° C. | 60.27 | 52.4 | 3.63 | 3.37 | 4.4 | 3.36 |

TABLE I-continued

Compounds of the Formula:

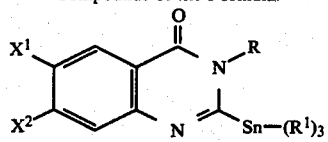

| Compound No. | X¹ | X² | R | R¹ | Physical State | %C Calc. | %C Found | %H Calc. | %H Found | %N Calc. | %N Found |
|---|---|---|---|---|---|---|---|---|---|---|---|
| 19 45788 | —Cl | —H | (phenyl) | (phenyl) | White solid, mp 186–188° C. | 60.08 | 61.62 | 3.94 | 3.87 | 4.38 | 5.56 |

TABLE II

| Compound No. | Bactericidal Activity Pseudo. | Erwin. | Xanth. |
|---|---|---|---|
| 1 46169 | 0 | 0 | 100 |
| 2 46388 | 14 | 0 | 100 |
| 3 46360 | 0 | 0 | 0 |
| 4 46359 | 0 | 0 | 100 |
| 5 45331 | 0 | 0 | 63 |
| 6 45330 | 0 | 0 | 0 |
| 7 45228 | 0 | 0 | 50 |
| 8 46358 | 0 | 0 | 100 |
| 9 46357 | 0 | 0 | 21 |
| 10 46356 | 0 | 0 | 100 |
| 11 45916 | 0 | 0 | 100 |
| 12 45915 | 0 | 0 | 21 |
| 13 45913 | 0 | 0 | 100 |
| 14 45301 | 0 | 0 | 0 |
| 15 45300 | 0 | 0 | 38 |
| 16 46151 | 0 | 0 | 100 |
| 17 46150 | 0 | 0 | 0 |
| 18 46166 | 0 | 0 | 100 |
| 19 45788 | 0 | 0 | 88 |

TABLE IV

| Compound No. | AR | AW | HF | MA | ME | Aph. | AS | CL | 5-CL |
|---|---|---|---|---|---|---|---|---|---|
| 1 46169 | 0 | — | 0 | 0 | 0 | 0 | 0 | 0 | 70 |
| 2 46388 | 85 | — | 92 | 100 | 95 | 80 | 0 | — | — |
| 3 46360 | 0 | — | 0 | 90 | 90 | 0 | 0 | 70 | 90 |
| 4 46359 | 0 | — | -0 | 0 | 0 | 0 | 0 | 0 | 90 |
| 5 45331 | 0 | — | 40 | — | 95 | 0 | 0 | 10 | 100 |
| 6 45330 | 0 | — | 0 | 0 | 0 | 0 | 0 | 0 | 0 |
| 7 45228 | 0 | — | 0 | 0 | 0 | 0 | 0 | 0 | 60 |
| 8 46358 | 0 | — | 0 | 100 | 100 | 0 | 0 | 50 | 80 |
| 9 46357 | 0 | — | 0 | 100 | 0 | 0 | 0 | 100 | 90 |
| 10 46356 | 0 | — | 0 | 0 | 0 | 0 | 0 | 0 | 100 |
| 11 45916 | 70 | — | 75 | 99 | 100 | 80 | 0 | 0 | 100 |
| 12 45915 | 0 | — | 0 | 95 | 100 | 0 | 0 | 0 | 60 |
| 13 45913 | 0 | — | 0 | 90 | 80 | 0 | 0 | 0 | 90 |
| 14 45301 | 0 | — | 0 | 0 | 0 | 0 | 0 | 0 | 0 |
| 15 45300 | 0 | — | 0 | 0 | 0 | 0 | 0 | 0 | 0 |
| 16 46151 | 90 | — | — | 100 | 100 | 95 | — | 0 | 50 |
| 17 46150 | 0 | — | 0 | 90 | 100 | 0 | — | 0 | 30 |
| 18 46166 | 0 | — | 0 | 0 | 50 | 0 | 0 | 0 | 100 |

TABLE III

| Compound No. | Pyth. | Rhiz. | Fusar. | Botry. | Asper. | Ustil. | TLB | RB | TEB | CLB | BPM | BR |
|---|---|---|---|---|---|---|---|---|---|---|---|---|
| 1 46169 | 15 | 30 | 0 | 26 | 53 | 0 | 91 | 80 | 17 | 100 | 100 | 0 |
| 2 46388 | 37 | 55 | 86 | 31 | 116 | 37 | 100 | 75 | 0 | 100 | 64 | 0 |
| 3 46360 | 0 | 27 | 38 | 0 | 100 | 15 | 98 | 0 | 0 | 100 | 100 | 0 |
| 4 46359 | 41 | 42 | 35 | 0 | 158 | 0 | 94 | 0 | 0 | 100 | 100 | 0 |
| 5 45331 | 54 | 0 | 77 | 16 | 82 | 0 | 100 | 88 | 0 | 100 | 100 | 0 |
| 6 45330 | 0 | 0 | 0 | 0 | 0 | 0 | 0 | 0 | 0 | 0 | 0 | 0 |
| 7 45228 | 35 | 50 | 51 | 35 | 82 | 31 | 94 | 91 | 0 | 95 | 100 | 0 |
| 8 46358 | 22 | 36 | 48 | 22 | 158 | 25 | 99 | 0 | 0 | 100 | 0 | — |
| 9 46357 | 0 | 0 | 42 | 0 | 69 | 14 | 98 | 0 | 0 | 100 | 100 | 0 |
| 10 46356 | 29 | 42 | 35 | 0 | 141 | 0 | 94 | 0 | 0 | 100 | 100 | 0 |
| 11 45916 | 100 | 33 | 75 | 30 | 119 | 39 | 100 | 50 | — | 100 | 100 | 0 |
| 12 45915 | 100 | 0 | 42 | 0 | 69 | 25 | 69 | 0 | 98 | 97 | 100 | 0 |
| 13 45913 | 88 | 0 | 0 | 0 | 81 | 25 | 31 | 33 | 0 | 98 | 100 | 0 |
| 14 45301 | 0 | 0 | 0 | 0 | 0 | 0 | 0 | 70 | — | 100 | 0 | 0 |
| 15 45300 | 40 | 0 | 96 | 38 | 67 | 0 | 72 | 65 | — | 100 | 100 | 0 |
| 16 46151 | 15 | 93 | 36 | 21 | 126 | 15 | 90 | 0 | 0 | 98 | 21 | 0 |
| 17 46150 | 35 | 0 | 0 | 0 | 0 | 0 | 0 | 0 | 0 | 90 | 100 | 0 |
| 18 46166 | 22 | 28 | 0 | 19 | 43 | 0 | 88 | 68 | 58 | 100 | 100 | 0 |
| 19 45788 | 28 | 23 | 0 | 0 | 0 | 0 | 59 | — | 62 | 99 | 100 | 0 |

Pyth. = *Pythium ultimum*
Rhiz. = *Rhizoctonia solani*
Fusar. = *Fusarium moniloforme*
Botry. = *Botrytis cinerea*
Asper. = *Aspergillus niger*
Ustil. = *Ustilago hordeii*
TLB = Tomato Late Blight
RB = Rice Blast
TEB = Tomato Early Blight
CLB = Celery Late Blight
BPM = Bean Powdery Mildew
BR = Bean Rust
— = Not Tested or Test Failed

TABLE IV-continued

| Insecticidal and Miticidal Activity | | | | | | | | | |
|---|---|---|---|---|---|---|---|---|---|
| Compound No. | | AR | AW | HF | MA | ME | Aph. | AS | CL | 5-CL |
| 19 | 45788 | 0 | — | 0 | 80 | 30 | 0 | 0 | 30 | 100 |

AR = American Cockroach
AW = Alfalfa Weevil
HF = Housefly
MA = Mite Adult
Aph. = Aphid
AS = Aphid Systemic
CL = Cabbage Looper
5-CL = 5-Day Reading of Cabbage Looper Mortality
— = Not Tested or Test Failed

TABLE V

| | | Herbicidal Activity | | | | | | | | | | | | | | |
|---|---|---|---|---|---|---|---|---|---|---|---|---|---|---|---|---|
| Compound No. | | LQ | MUS | PGW | BG | CG | WO | SB | R | LQ | MUS | PGW | BG | CG | WO | SB | R |
| 1 | 46169 | 0 | 0 | 0 | 0 | 0 | 0 | 0 | 0 | 30 | 30 | 0 | 0 | 0 | 0 | 30 | 0 |
| 2 | 46388 | 0 | 0 | 0 | 0 | 0 | 0 | 0 | 0 | 45 | 93 | 55 | 25 | 20 | 0 | 40 | 0 |
| 3 | 46360 | 0 | 0 | 0 | 0 | 0 | 0 | 0 | 0 | 0 | 0 | 0 | | 0 | 0 | 0 | 0 |
| 4 | 46359 | 0 | 0 | 0 | 0 | 0 | 0 | 0 | 0 | 25 | 25 | 20 | 0 | 0 | 0 | 30 | 0 |
| 5 | 45331 | 0 | 0 | 0 | 0 | 0 | 0 | 0 | 0 | 10 | 45 | 30 | 0 | 0 | 0 | 30 | 0 |
| 6 | 45330 | 0 | 0 | 0 | 0 | 0 | 0 | 0 | 0 | 0 | 0 | 0 | 0 | 0 | 0 | 0 | 0 |
| 7 | 45228 | 0 | 0 | 0 | 0 | 0 | 0 | 0 | 0 | 20 | 35 | 30 | 0 | 0 | 0 | 30 | 0 |
| 8 | 46358 | 0 | 0 | 0 | 0 | 0 | 0 | 0 | 0 | 40 | 95 | 93 | 50 | 30 | 20 | 70 | 0 |
| 9 | 46357 | 0 | 0 | 0 | 0 | 0 | 0 | 0 | 0 | 0 | 0 | 0 | 0 | 0 | 0 | 15 | 0 |
| 10 | 46356 | 0 | 0 | 0 | 0 | 0 | 0 | 0 | 0 | 30 | 60 | 40 | 0 | 0 | 0 | 35 | 0 |
| 11 | 45916 | 0 | 0 | 0 | 0 | 0 | 0 | 0 | 0 | 70 | 100 | 99 | 40 | 30 | 30 | 50 | 20 |
| 12 | 45915 | 0 | 0 | 0 | 0 | 0 | 0 | 0 | 0 | 0 | 0 | 40 | 0 | 0 | 0 | 25 | 0 |
| 13 | 45913 | 0 | 0 | 0 | 0 | 0 | 0 | 0 | 0 | 55 | 95 | 40 | 30 | 30 | 20 | 35 | 0 |
| 14 | 45301 | 0 | 0 | 0 | 0 | 0 | 0 | 0 | 0 | 0 | 0 | 0 | 0 | 0 | 0 | 0 | 0 |
| 15 | 45300 | 0 | 0 | 0 | 0 | 0 | 0 | 0 | 0 | 0 | 0 | 0 | 0 | 0 | 0 | 0 | 0 |
| 16 | 46151 | 0 | 0 | 0 | 0 | 0 | 0 | 0 | 0 | 50 | 100 | 80 | 0 | 0 | 0 | 40 | 0 |
| 17 | 46150 | — | — | — | — | — | — | — | — | — | — | — | — | — | — | — | — |
| 18 | 46166 | 0 | 0 | 0 | 0 | 0 | 0 | 0 | 0 | 30 | 100 | 30 | 0 | 0 | 0 | 70 | 0 |
| 19 | 45788 | 70 | 50 | 60 | 55 | 85 | 30 | 0 | 0 | 40 | 90 | 25 | 20 | 0 | 0 | 0 | 0 |

LQ = Lambsquarter
MUS = Mustard
PGW = Pigweed
BG = Barnyard Grass
CG = Crabgrass
WO = Wild Oat
SB = Soybean
R = Rice
— = Not Tested or Test Failed

What is claimed is:

1. A compound of the formula:

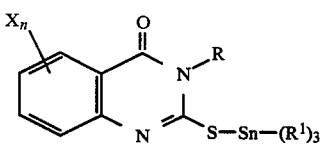

(I)

wherein X is independently halogen, lower alkyl of 1 to 6 carbon atoms, lower alkoxy of 1 to 6 carbon atoms, nitro, lower alkylsulfinyl of 1 to 6 carbon atoms, lower alkylthio of 1 to 6 carbon atoms, amino or trifluoromethyl; n is 0, 1, 2 or 3; R is hydrogen, alkyl of 1 to 10 carbon atoms, cycloalkyl of 3 to 8 carbon atoms, lower alkenyl of 2 to 6 carbon atoms, or lower alkynyl of 2 to 6 carbon atoms, all optionally substituted with 1 to 3 of the same or different halogen atoms; or aryl of 6 to 12 carbon atoms; or substituted aryl substituted with 1 to 3 substituents independently selected from lower alkyl of 1 to 4 carbon atoms, lower alkoxy of 1 to 4 carbon atoms, and the group —$S(O)_k R^2$ where k is 0, 1 or 2 and $R^2$ is lower alkyl of 1 to 4 carbon atoms, nitro, cyano or halogen; and $R^1$ is lower alkyl of 1 to 6 carbon atoms, lower cycloalkyl of 3 to 8 carbon atoms or aryl of 6 to 12 carbon atoms; provided that R and $R^1$ are not both cyclohexyl.

2. A compound according to claim 1 wherein R is hydrogen, lower alkyl, phenyl or substituted phenyl.

3. A compound according to claim 2 wherein $R^1$ is phenyl.

4. A compound according to claim 3 wherein X is chloro, nitro, trifluoromethyl or methyl.

5. A compound according to claim 4 wherein n is 0.

6. A compound according to claim 5 wherein R is hydrogen.

7. A compound according to claim 5 wherein R is n-butyl.

8. A compound according to claim 5 wherein R is phenyl.

9. A compound according to claim 5 wherein R is methyl.

10. A compound according to claim 3 wherein n is 1.

11. A compound according to claim 10 wherein X is chloro.

12. A compound according to claim 11 wherein R is phenyl.

13. A compound according to claim 12 wherein $R^1$ is n-butyl.

14. A compound according to claim 13 wherein R is phenyl.

15. A compound according to claim 14 wherein n is 0.

16. A compound according to claim 14 wherein n is 1.

17. A compound according to claim 16 wherein X is 7-chloro.

18. A method of controlling fungi which comprises contacting said fungi or their growth environment with a fungicidally effective amount of a compound of claim 1.

19. A method of controlling fungi which comprises contacting said fungi or their growth environment with a fungicidally effective amount of a compound of claim 2.

20. A method of controlling fungi which comprises contacting said fungi or their growth environment with a fungicidally effective amount of a compound of claim 3.

21. A method of controlling fungi which comprises contacting said fungi or their growth environment with a fungicidally effective amount of a compound of claim 5.

22. A method of controlling fungi which comprises contacting said fungi or their growth environment with a fungicidally effective amount of a compound of claim 7.

23. A method of controlling fungi which comprises contacting said fungi or their growth environment with a fungicidally effective amount of a compound of claim 8.

24. A method of controlling fungi which comprises contacting said fungi or their growth environment with a fungicidally effective amount of a compound of claim 9.

25. A method of controlling fungi which comprises contacting said fungi or their growth environment with a fungicidally effective amount of a compound of claim 12.

26. A method of controlling fungi which comprises contacting said fungi or their growth environment with a fungicidally effective amount of a compound of claim 15.

27. A fungicidal composition which comprises an inert carrier and a fungicidally effective amount of a compound of claim 1.

28. A fungicidal composition which comprises an inert carrier and a fungicidally effective amount of a compound of claim 2.

29. A fungicidal composition which comprises an inert carrier and a fungicidally effective amount of a compound of claim 3.

30. A fungicidal composition which comprises an inert carrier and a fungicidally effective amount of a compound of claim 5.

31. A fungicidal composition which comprises an inert carrier and a fungicidally effective amount of a compound of claim 7.

32. A fungicidal composition which comprises an inert carrier and a fungicidally effective amount of a compound of claim 8.

33. A fungicidal composition which comprises an inert carrier and a fungicidally effective amount of a compound of claim 9.

34. A fungicidal composition which comprises an inert carrier and a fungicidally effective amount of a compound of claim 12.

35. A fungicidal composition which comprises an inert carrier and a fungicidally effective amount of a compound of claim 15.

36. A method of killing acarines which comprises contacting said acarine or its environment with an acaricidally effective amount of a compound of claim 14.

37. A method of killing acarines which comprises contacting said acaraine or its environment with an acaricidally effective amount of a compound of claim 16.

38. An acaricidal composition which comprises a biologically inert carrier and an acaricidally effective amount of a compound of claim 14.

39. An acaricidal composition which comprises a biologically inert carrier and an acaricidally effective amount of a compound of claim 16.

* * * * *